United States Patent von Kries et al.

[11] Patent Number: 5,945,299
[45] Date of Patent: Aug. 31, 1999

[54] PRODUCTION OF WHEAT PROTEIN HYDROLYZATES BY MULTISTAGE HYDROLYSIS WITH A PROTEINASE AND PEPTIDASE

[75] Inventors: Edith von Kries, Illertissen; Andrea Heilemann, Ulm; Andreas Sander, Illertissen, all of Germany

[73] Assignee: Henkel Kommanditgesellschaft Auf Aktien (KGaA), Duesseldorf, Germany

[21] Appl. No.: 08/875,677

[22] PCT Filed: Jan. 16, 1996

[86] PCT No.: PCT/EP96/00147

§ 371 Date: Oct. 6, 1997

§ 102(e) Date: Oct. 6, 1997

[87] PCT Pub. No.: WO96/22699

PCT Pub. Date: Aug. 1, 1996

[30] Foreign Application Priority Data

Jan. 25, 1995 [DE] Germany .......................... 195 02 168

[51] Int. Cl.⁶ ...................... C12P 21/06; A23J 1/12
[52] U.S. Cl. ............................. 435/68.1; 426/52
[58] Field of Search .............. 435/68.1; 426/49, 426/52

[56] References Cited

U.S. PATENT DOCUMENTS

| | | | |
|---|---|---|---|
| 4,138,500 | 2/1979 | Fulger et al. | 426/46 |
| 4,282,319 | 8/1981 | Conrad | 435/69 |
| 4,377,602 | 3/1983 | Conrad | 426/656 |
| 4,757,007 | 7/1988 | Satoh et al. | 435/69 |
| 5,554,508 | 9/1996 | Auriol et al. | 435/68.1 |
| 5,602,002 | 2/1997 | Eilers et al. | 435/68.1 |

FOREIGN PATENT DOCUMENTS

| | | |
|---|---|---|
| 0 187 048 | 7/1986 | European Pat. Off. . |
| 0 298 419 | 1/1989 | European Pat. Off. . |
| 0 325 986 | 8/1989 | European Pat. Off. . |
| 0 363 771 | 4/1990 | European Pat. Off. . |
| 0 495 391 | 7/1992 | European Pat. Off. . |
| 0 578 572 | 1/1994 | European Pat. Off. . |
| 2 406 665 | 5/1979 | France . |
| 2 542 013 | 9/1984 | France . |
| 2 688 229 | 9/1993 | France . |
| 41 16 744 | 11/1992 | Germany . |
| 44 10 000 | 3/1995 | Germany . |
| 63/216438 | 9/1988 | Japan . |
| 1-300854 | 12/1989 | Japan . |
| 21/01016 | 4/1990 | Japan . |
| 52/27983 | 9/1993 | Japan . |
| WO92/15696 | 9/1992 | WIPO . |

OTHER PUBLICATIONS

Ärztl. Kosmetol., 13:524 (1983).
Parfüm. Kosmet., 66:85 (1985).
Cosmet. Toil., 99(12):63–74 (1984).

*Primary Examiner*—David M. Naff
*Attorney, Agent, or Firm*—Ernest G. Szoke; Wayne C. Jaeschke; Glenn E. J. Murphy

[57] ABSTRACT

Wheat protein hydrolyzates are produced by hydrolyzing a wheat protein-containing starting material, preferably a wheat protein isolate having a protein content of 70 to 90%, with a proteinase such as a serine protease at a pH of 2 to 5, then with a proteinase at a pH of 8 to 10 and finally with a peptidase at a pH of 6 to 7. The hydrolysis steps are preferably at a temperature below the gelatinization temperature of carbohydrate present in the protein. Each hydrolysis may be carried out for 1 to 24 hours at a temperature of 40 to 70° C. To reduce traces of unwanted color formers, an adsorbent such as silica gel, aluminum oxide or activated carbon may be present during the hydrolysis steps. Aqueous wheat protein hydrolyzate solutions are obtained and, if required, may be concentrated, for example using falling film evaporators. The hydrolyzates have an average molecular weight in the range of 100 to 30,000, preferably 2,000 to 5,000, and a solids content of around 5 to 50%. The hydrolyzates may be condensed with a fatty acid or a fatty acid chloride containing 6 to 22 carbons such as lauric acid or coconut oil fatty acid to produce light-colored, storage-stable derivatives.

15 Claims, No Drawings

PRODUCTION OF WHEAT PROTEIN HYDROLYZATES BY MULTISTAGE HYDROLYSIS WITH A PROTEINASE AND PEPTIDASE

BACKGROUND OF THE INVENTION

1. Field of the Invention

This invention relates to a process for the production of wheat protein hydrolyzates, in which the multistage hydrolysis is carried out in the presence of selected enzymes, and to the use of the hydrolyzates for the production of light-colored, storage-stable derivatives.

2. Discussion of the Related Art

Degradation products of polypeptides, so-called protein hydrolyzates, have been known for some time. Although they do not have any detergent properties because of the absence of a lipophilic group, they are used in a large number of surface-active formulations by virtue of their dispersing properties and their ability favorably to influence the dermatological compatibility of anionic surfactants by interaction with the protein molecules of the skin. Relevant synoptic articles have been published, for example, by A. Domsch et al. in Ärztl. Kosmetol. 13, 524 (1983), by G. Schuster et al. in Cosmet. Toil., 99(12), 63–74 (1984) and by H. Lindner in Parfüm. Kosmet., 66, 85 (1985).

Protein hydrolyzates are normally obtained on the basis of animal collagen. In recent years, however, there has been an increasing trend towards vegetable products, for example based on wheat gluten or soya protein.

For example, the hydrolysis of vegetable proteins by special lactic acid bacteria in the presence of hydrocarbons is known from FR-A 25 42 013 (ABC). U.S. Pat. No. 4,757,007 (Nisshin) describes the partial hydrolysis of soya proteins with proteases into fractions differing in their solubility in trichloro-acetic acid, separation of the fractions at a pH value of 7, removal of non-hydrolyzed components and purification of the products by ultrafiltration. European patent application EP-A-0 187 048 (Novo) describes the enzymatic degradation of soya proteins by treatment with special proteases. The production of protein hydrolyzates with an average molecular weight of 500 to 90,000 by step-by-step alkaline, acidic and/or enzymatic degradation of wheat or soya proteins is known from EP-A 0 298 419 (Katayama). Finally, EP-A 0 363 771 (Nestle) reports on a process for the production of protein hydrolyzates in which vegetable proteins are hydrolyzed with hydrochloric acid, non-hydrolyzed components are removed, the hydrolyzates are alkalized to destroy unwanted chlorinated compounds and the resulting products are subsequently acidified.

However, one feature common to all known processes is that, when applied to the vegetable raw material wheat, they give products which, after chemical derivatization, for example after condensation with fatty acid chlorides, discolor and are not sufficiently stable in storage. One particular problem is, for example, that fatty acid condensates of known wheat protein hydrolyzates show an unwanted tendency to cloud in aqueous solution.

Accordingly, the object of the present invention was to provide a solution to the problem of the inadequate stability in storage of derivatives based on wheat protein hydrolyzates.

DESCRIPTION OF THE INVENTION

The present invention relates to a process for the production of wheat protein hydrolyzates in which protein-containing starting materials are hydrolyzed first with proteinases and then with peptidases.

After extensive studies, applicants have found that the inadequate stability of the derivatives in storage is attributable to an unfavorable molecular weight distribution of the precursor, i.e. the wheat protein hydrolyzates. Accordingly, the solution to the problem in question had to be directed at the wheat protein hydrolyzate stage. It was surprisingly found that enzymatic degradation using carefully selected enzymes leads to hydrolyzates which, in turn, provide storage-stable derivatives and, more particularly, wheat protein fatty acid condensates which do not cloud in the form of an aqueous solution.

Three-stage enzymatic degradation

In one preferred embodiment of the process according to the invention, protein-containing starting materials, preferably wheat gluten, and corresponding chemically or enzymatically modified derivatives are (a) treated with proteinases first at a pH value of 2 to 5 and
(b) then at a pH value of 8 to 10 and
(c) finally, are hydrolyzed with peptidases at a pH value of 6 to 7.

In the context of the invention, protein-containing starting materials are understood to be protein isolates which are obtained, for example, by extraction of wheat flour using known methods and which may have a protein content of 70 to 90% by weight.

Proteinases and peptidases

Proteinases and peptidases belong to the group of proteases, i.e. enzymes, which catalyze the hydrolytic cleavage of the peptide bond and, accordingly, belong systematically to the hydrolases. Proteinases, which are also known as endoproteases or endopeptidases, cleave peptide bonds within the protein. They are different from the (exo) peptidases which promote degradation of the terminal peptide bond of the terminal amino or carboxyl group.

Typical examples of proteinases suitable for the purposes of the process according to the invention are the commercially available serine proteinases (EC 3.4.21), cysteine or thiol proteinases (EC 3.4.22), acidic proteinases of the aspartate or carboxyproteinase type (EC 3.4.23) and —subordinately—metal proteinases (3.4.24). Examples of suitable serine proteinases are chymotrypsin, elastase, kallikrein, plasmin, trypsin, thrombin and subtilisin.

Suitable peptidases include, for example, the α-aminoacyl peptide hydrolases or aminopeptidases (EC 3.4.11), which detach individual amino acids at the end of the polypeptide, the dipeptide hydrolases or dipeptidases (EC 3.4.13), which hydrolyze dipeptides to amino acids, the dipeptidyl peptide hydrolases or dipeptidyl peptidases (EC 3.4.14), which release the dipeptides in the amino position of a polypeptide, peptidyl dipeptide hydrolases or dipeptidyl carboxypeptidases (EC 3.4.15), which separate individual amino acids of the carboxy terminus, carboxypeptidases (EC 3.4.16–3.4.18) and ω-peptidases (EC 3.4.19) which split off modified amino acids from both ends of the polypeptide.

Basically, the quantity in which the proteinases or peptidases are used is not critical although the quantities used should be in the range from 0.1 to 5% by weight and preferably in the range from 0.5 to 2% by weight, based on the starting materials.

Adsorbents

To remove traces of unwanted color formers, it has proved to be of advantage to introduce the protein-containing starting materials into the hydrolysis process together with suitable adsorbents. Suitable adsorbents are, for example, silica gels, aluminium oxides and—preferably—activated carbons which may be used in quantities of 0.1 to 15% by weight and preferably in quantities of 1 to 5% by weight, based on the nitrogen content of the protein-containing starting materials.

Carrying out the hydrolysis process

To carry out the enzymatic hydrolysis, an aqueous suspension of the protein-containing starting material—optionally together with the adsorbents described above—is degraded for 1 to 24 h at the optimum temperature and pH value of the proteinases and peptidases used, for example at 40 to 70° C. It is of particular advantage to carry out the hydrolysis below the gelatinization temperature of the carbohydrates still present in the protein.

If the hydrolysis is carried out in the presence of calcium oxide or calcium hydroxide as base, soluble calcium peptides are formed and have to be separated from the undissolved calcium oxide or calcium hydroxide by filtration. If the alkali peptides are required, it is advisable to treat the calcium peptides with soda or potash solution and then to remove the poorly soluble calcium carbonate. The calcium may also be precipitated in the form of calcium sulfate or calcium oxalate. The poorly soluble salts are preferably removed by standard separation techniques for solid/liquid separation, such as filtration, separation and the like, preferably in the presence of filter aids.

Aqueous wheat protein hydrolyzate solutions are obtained and, if required, may be concentrated, for example using falling film evaporators. The hydrolyzates obtainable by the process according to the invention have an average molecular weight in the range from 100 to 30,000, preferably in the range from 100 to 10,000 and more preferably in the range from 2,000 to 5,000 and a solids content of around 5 to 50% by weight.

Commercial Applications

The vegetable wheat protein hydrolyzates obtainable by the process according to the invention are distinguished by particularly favorable color quality and, after derivatization, give substances which show particularly high stability in storage in aqueous solution. In particular, fatty acid condensates based on the wheat protein hydrolyzates obtainable by the process according to the invention can be processed to clear storage-stable aqueous solutions.

Accordingly, the present invention also relates to the use of the wheat protein hydrolyzates obtainable by the process according to the invention for the production of light-colored, storage-stable derivatives such as, for example, N-acylated, N-alkylated, esterified derivatives and N-acylated or N-alkylated and, in addition, esterified derivatives.

The wheat protein hydrolyzates obtainable by the process according to the invention are preferably condensed in known manner with fatty acids or fatty acid chlorides containing 6 to 22 and, more particularly, 12 to 18 carbon atoms. The wheat protein hydrolyzates are used with particular preference for the production of lauric acid or coconut oil fatty acid condensates.

The following Examples are intended to illustrate the invention without limiting it in any way.

EXAMPLES

Example 1

3,500 l of warm water ($T_{max}$=50° C.) were introduced into a 5 m³ stirred tank reactor and 1.3 kg of sodium sulfite and 14 kg of activated carbon were subsequently added. 650 kg of wheat protein isolate were added at 48–50° C. while stirring at maximum speed and the whole was stirred to form a suspension. The pH value of the reaction mixture was then adjusted to pH 3.0 by addition of hydrochloric acid.

5 kg of proteinase with an optimum pH in the acidic range were then added. During the hydrolysis and the subsequent first filtration, the temperature was limited to a maximum of 50° C. and the sulfite concentration was kept above 10 ppm. The pH value was initially kept at 3.0 by addition of hydrochloric acid and, after 2 h, was adjusted to 8.5 by addition of calcium hydroxide. At the same time, another 14 kg of activated carbon and 5 kg of proteinase with an optimum pH in the alkaline range were added. The reaction mixture was then stirred for another 2 h at around 50° C. with no further pH correction. After the enzymatic hydrolysis steps, the pH value of the mixture was adjusted to 7.5 by addition of calcium hydroxide. The hydrolyzate thus prepared was filtered in a filter press after addition of 70 kg of a filter aid (Perlite® P 50).

20 kg of Carbopal® GnA were then added to the filtrate, followed by heating to 80° C. This temperature was maintained for 15 minutes. The reaction mixture was then cooled to 50° C. and stirred at that temperature for 30 minutes. After addition of another 15 kg of the filter aid, the product was refiltered in a filter press. Finally, the calcium was precipitated by addition of soda and the calcium carbonate was removed in a filter press. The filtrate was concentrated to a content of 44% Brix in a falling-film evaporator. Finally, the concentrate was adjusted with sodium hydroxide to a pH value of 10 and, after storage for 5 days, was filtered in a filter press in the presence of 15 kg of filter aid.

Example 2

10 kg of the wheat protein hydrolyzate prepared in accordance with Example 1 were acylated in known manner with lauric acid chloride. The reaction product was adjusted to a dry matter content of 20% by weight and was stored for 3 weeks at 20° C. and 40° C. After the period of storage, the product was clear at both temperatures and was substantially the same color.

Comparison Example 1

A commercial wheat protein hydrolyzate was acylated with lauric acid chloride as described in Example 2. A 20% by weight solution of the resulting wheat protein fatty acid condensate clouded after storage for only 1 week.

We claim:

1. A process for the production of a wheat protein hydrolyzate comprising the steps of:
   (a) hydrolyzing a wheat protein-containing starting material with a proteinase at a pH of 2 to 5;
   (b) further hydrolyzing the product of step (a) with a proteinase at a pH of 8 to 10; and
   (c) further hydrolyzing the product of step (b) with a peptidase at a pH of 6 to 7.

2. A process according to claim 1, wherein the hydrolysis steps occur in the presence of activated carbon.

3. A process according to claim 1, wherein the hydrolysis steps are carried out at a temperature below the gelatinization temperature of carbohydrates present in the protein.

4. A process according to claim 2, wherein the hydrolysis steps are carried out at a temperature below the gelatinization temperature of carbohydrates present in the protein.

5. A process according to claim 1, further comprising condensing the product of step (c) with a fatty acid or fatty acid chloride having 6 to 22 carbon atoms.

6. A process according to claim 2, further comprising condensing the product of step (c) with a fatty acid or fatty acid chloride having 6 to 22 carbon atoms.

7. A process according to claim 3, further comprising condensing the product of step (c) with a fatty acid or fatty acid chloride having 6 to 22 carbon atoms.

8. A process according to claim 4, further comprising condensing the product of step (c) with a fatty acid or fatty acid chloride having 6 to 22 carbon atoms.

9. A process for production of a wheat protein hydrolyzate from a wheat protein-containing starting material, said starting material having a protein content of 70% to 90% by weight, said process comprising:

(a) hydrolyzing said wheat protein-containing starting material in an aqueous suspension at a pH of 2 to 5 with 0.1% to 5% by weight, based on the starting material, of a proteinase;

(b) further hydrolyzing the product of step (a) in an aqueous suspension at a pH of 8 to 10 with 0.1% to 5% by weight, based on the starting material, of a proteinase; and (c) further hydrolyzing the product of step (b) in an aqueous suspension at a pH of 6 to 7 with 0.1% to 5% by weight, based on the starting material, of a peptidase, wherein the proteinases are enzymes selected from the group of enzyme classes consisting of EC 3.4.21, EC 3.4.22 EC 3.4.23, a and EC 3.4.24, and the peptidase is an enzyme selected from the group of enzyme classes consisting of EC 3.4.11, EC 3.4.13, EC 3.4.14, EC 3.4.15, EC 3.4.16, EC 3.4.17, EC 3.4.18, and EC 3.4.19.

10. A process according to claim 9, wherein the proteinase is a serine proteinase selected from the group consisting of chymotrypsin, elastase, kallikrein, plasmin, trypsin, thrombin, and subtilisin.

11. A process according to claim 9, wherein the hydrolysis steps (a) to (c) are carried out with 0.5% to 2% by weight of proteinase or peptidase.

12. A process according to claim 9, wherein the aqueous suspension contains 0.1% to 15% by weight, based on nitrogen content of the protein-containing starting material, of an adsorbent selected from the group consisting of silica gels, aluminum oxides, and activated carbons.

13. A process according to claim 9, wherein each hydrolysis step is carried out for 1 to 24 hours at a temperature of 40 to 70° C.

14. A process according to claim 9, wherein each hydrolysis step is carried out at a temperature below the gelatinization temperature of carbohydrates present in the protein.

15. A process according to claim 9, wherein the wheat protein hydrolyzate from step (c) is condensed with a fatty acid or a fatty acid chloride having 6 to 22 carbon atoms.

\* \* \* \* \*